(12) United States Patent
Yamanis et al.

(10) Patent No.: US 9,120,683 B2
(45) Date of Patent: Sep. 1, 2015

(54) METHOD AND DEVICE USING A CERAMIC BOND MATERIAL FOR BONDING METALLIC INTERCONNECT TO CERAMIC ELECTRODE

(75) Inventors: Jean Yamanis, South Glastonbury, CT (US); Dustin Frame, Glastonbury, CT (US); Lei Chen, South Windsor, CT (US); Ellen Y. Sun, South Windsor, CT (US)

(73) Assignee: Ballard Power Systems Inc., Burnaby (CA)

( * ) Notice: Subject to any disclaimer, the term of this patent is extended or adjusted under 35 U.S.C. 154(b) by 377 days.

(21) Appl. No.: 13/577,327

(22) PCT Filed: Feb. 8, 2010

(86) PCT No.: PCT/US2010/023448
§ 371 (c)(1),
(2), (4) Date: Aug. 6, 2012

(87) PCT Pub. No.: WO2011/096939
PCT Pub. Date: Aug. 11, 2011

(65) Prior Publication Data
US 2012/0295183 A1 Nov. 22, 2012

(51) Int. Cl.
*H01M 8/02* (2006.01)
*C01G 51/00* (2006.01)
*H01M 4/86* (2006.01)
(Continued)

(52) U.S. Cl.
CPC ............. *C01G 51/00* (2013.01); *H01M 4/8621* (2013.01); *H01M 4/8657* (2013.01); *H01M 8/0206* (2013.01); *H01M 8/0228* (2013.01); *H01M 8/0297* (2013.01); *H01M 8/1213* (2013.01); *C01P 2002/32* (2013.01); *C01P 2002/34* (2013.01); *C01P 2002/52* (2013.01); *C01P 2006/40* (2013.01); *G01N 27/407* (2013.01); *H01M 4/8889* (2013.01);
(Continued)

(58) Field of Classification Search
CPC .......................... H01M 8/0297; H01M 8/1213
USPC .................................................... 429/400–535
See application file for complete search history.

(56) References Cited

U.S. PATENT DOCUMENTS 5,290,642 A 3/1994 Minh
2003/0224232 A1* 12/2003 Browall et al. ................. 429/30
(Continued)

FOREIGN PATENT DOCUMENTS

EP 1786056 5/2007

OTHER PUBLICATIONS

Yang, Z., G. Xia, X. Li, and J. Stevenson. "(Mn,Co)3O4 Spinel Coatings on Ferritic Stainless Steels for SOFC Interconnect Applications." International Journal of Hydrogen Energy 32.16 (2007): 3648-654.*

(Continued)

*Primary Examiner* — Kenneth Douyette
*Assistant Examiner* — James Lee
(74) *Attorney, Agent, or Firm* — Seed IP Law Group PLLC

(57) ABSTRACT

An electrochemical device includes a ceramic electrode, a metallic interconnect, and a ceramic bond material that bonds the ceramic electrode and the metallic interconnect together. The ceramic material includes manganese-cobalt-oxide that is electrically conductive such that electric current can flow between the ceramic electrode and the metallic interconnect.

20 Claims, 2 Drawing Sheets

(51) Int. Cl.
*H01M 8/12* (2006.01)
*G01N 27/407* (2006.01)
*H01M 4/88* (2006.01)

(52) U.S. Cl.
CPC ........... *H01M 4/8896* (2013.01); *Y02E 60/521* (2013.01); *Y02E 60/525* (2013.01)

(56) References Cited

U.S. PATENT DOCUMENTS

2004/0214069 A1 10/2004 Seabaugh
2007/0072070 A1* 3/2007 Quek et al. ................... 429/149
2007/0111069 A1* 5/2007 Rehg et al. ..................... 429/32

OTHER PUBLICATIONS

International Search Report and Written Opinion for PCT/US2010/023448.

Transmittal of International Preliminary Report on Patentability, Aug. 23, 2012.

* cited by examiner

US 9,120,683 B2

METHOD AND DEVICE USING A CERAMIC BOND MATERIAL FOR BONDING METALLIC INTERCONNECT TO CERAMIC ELECTRODE

BACKGROUND OF THE DISCLOSURE

This disclosure relates to bonding ceramic electrodes to metallic interconnects. Devices such as fuel cells, sensors, and the like typically utilize a ceramic electrode in an electronic circuit with a metallic interconnect. For instance, the ceramic electrode may be bonded to the metallic interconnect using a relatively expensive noble metal. Noble metals are capable of withstanding severe operating environments, such as elevated temperatures and corrosive conditions (e.g., air and hydrogen in the case of a fuel cell).

However, one drawback associated with noble metals is potential damage to the device from thermal cycling (e.g., cycling the device between a low temperature, such as ambient, and a high temperature, e.g., 1000° C., and back under a range of ramping rates). The coefficient of thermal expansion of the ceramic electrode is considerably different than most noble metals or noble metal alloys. The difference in thermal expansion can cause thermal stresses that damage the device and ultimately reduce performance. Many potential replacement materials to the noble metal that have a coefficient of thermal expansion that matches the ceramic electrode are not suitable for forming a strong bond, do not have suitable electric conductivity, or have processing constraints relative to the other materials of the device that prevent implementation.

SUMMARY OF THE DISCLOSURE

An exemplary electrochemical device includes a ceramic electrode, a metallic interconnect, and a ceramic bond material that bonds the ceramic electrode and the metallic interconnect together. The ceramic material includes manganese-cobalt-oxide that is electrically conductive such that electric current can flow between the ceramic electrode and the metallic interconnect.

An exemplary method of processing an electrochemical device includes heating a ceramic electrode, a metallic interconnect, and a bonding material comprising ceramic precursors to a reaction temperature and then oxidizing and densifying the ceramic precursors to form a ceramic bond material that includes manganese-cobalt-oxide which bonds the ceramic electrode and the metallic interconnect together.

BRIEF DESCRIPTION OF THE DRAWINGS

The various features and advantages of the disclosed examples will become apparent to those skilled in the art from the following detailed description. The drawings that accompany the detailed description can be briefly described as follows.

DETAILED DESCRIPTION OF THE PREFERRED EMBODIMENT

Figure 1:
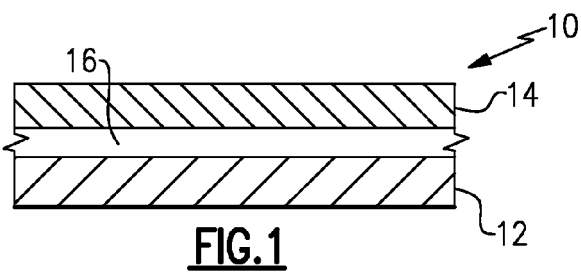
FIG. 1 illustrates an example electrochemical device that includes a ceramic bond material.

FIG. 1 schematically illustrates selected portions of an example device 10 (e.g., electrochemical device). As an example, the device 10 may be within a fuel cell assembly, oxygen sensor, solid oxide hydrogen generator, solid oxide oxygen generator, or the like.

The device 10 includes a ceramic electrode 12, a metallic interconnect 14, and a ceramic bond material 16 that bonds the ceramic electrode 12 and the metallic interconnect 14 together. In this case, the ceramic bond material 16 is located between the ceramic electrode 12 and the metallic interconnect 14 and is in direct contact with each. However, using additional layers between the ceramic electrode 12 and/or the metallic interconnect 14 and the ceramic bond material 16 is also contemplated.

As may be appreciated, the ceramic electrode 12 may be any type of electrode through which an electric current flows or is intended to flow. For instance, the ceramic electrode 12 is the cathode or air electrode in a solid oxide fuel cell. Likewise, the metallic interconnect is not limited to any particular type and may depend, for example, on the end use of the device 10. For instance, the metallic interconnect may be a porous wire mesh or include channels for delivering a reactant gas in a fuel cell.

The ceramic bond material 16 includes the ceramic material manganese-cobalt-oxide, which is electrically conductive such that an electric current can flow between the ceramic electrode 12 and the metallic interconnect 14. As an example, the manganese-cobalt-oxide may be of the spinel composition $Mn_{1.5}Co_{1.5}O_4$. The manganese-cobalt-oxide composition may alternatively be of the composition $Mn_2CoO_4$, $MnCo_2O_4$, or a mixture thereof.

The manganese-cobalt-oxide may also include a dopant or dopants that function to modify the properties of the manganese-cobalt-oxide. For example, a dopant may modify the electric properties of the ceramic bond material 16 or modify the processing properties of the bond material. The dopant material may include one or more rare earth (RE) elements or mixtures thereof, such as cerium. The rare earth elements may be in oxide form (REO). In one example, the cerium is in oxide form as ceria ($CeO_2$). The rare earth elements include scandium, yttrium, and the lanthanide elements and their oxide forms.

In another embodiment of the present invention, the manganese-cobalt-oxide for bond material 16 may also include a dopant or dopants that function to modify the properties of the manganese-cobalt-oxide. For example, a dopant may modify the electric properties of the ceramic bond material 16 or modify the processing properties of the bond material. The dopant material may include one or more transition metals selected from the group of iron, chromium, nickel, copper, and zinc and mixtures thereof. The aforementioned transition metals may be in the form of oxides.

In another embodiment of the present invention, the bond material 16 may be a composite material composed of a ceramic material and a noble metal, which may improve the bond strength as well as the electric conductivity of the composite material. The ceramic component moderates the thermal expansion coefficient of the composite bond material. The ceramic material of the composite bond material may be comprised of manganese cobalt oxide, with or without the aforementioned RE metal or REO and/or the aforementioned group of transition metals or their oxide forms and the noble metal may be selected from the group of silver, gold, platinum, or palladium. In one example, the noble metal is silver. The noble metal in the composite bond material may be a minor component, i.e., up to 35 volume %.

In some cases, the manganese-cobalt-oxide may include other minor phases. In some examples, the ceramic bond material 16 may include only the above example compositions and elements, with impurities or elements that are unmeasured or undetectable in the material and that do not affect the properties of the material. In a further example, the example ceramic bond material 16 includes only the given compositions/elements.

The materials of the ceramic electrode 12 and the metallic interconnect 14 may be materials that are suitable for the intended application. In general, the metallic interconnect 14 is made of a metal or metal alloy and the ceramic electrode 12 is made of a ceramic material, such as an oxide. In one example that is applicable to fuel cells (e.g., FIG. 2A or 2B), the ceramic electrode 12 is strontium-doped lanthanum manganite (LSM) and the metallic interconnect 14 is ferritic stainless steel. Ferritic stainless steel typically includes about 10.5-27 wt % chromium as the primary alloy element and a microstructure that is predominantly ferrite. Given this description, one of ordinary skill in the art will be able to recognize other ceramic materials and metals/metal alloys to suit their particular needs. Interconnect 14 may also be coated with appropriate ceramic oxide materials, such as spinels or perovskites, which help to minimize or eliminate chromium oxide evaporation and/or improve the oxidation resistance of the metallic interconnect 14. The coating ceramic materials may have compositions that mirror the spinel compositions taught herewith for the bonding materials. The metallic interconnect 14 may also be coated with electrically conductive ceramic oxides such as spinels and/or perovskites that may provide a means for mitigating chromia evaporation. Similarly, the metallic interconnect 14 may be coated with single metal or metal alloys, which after heat treatment convert to electrically conductive ceramic oxides such as spinels or perovskites. Potential metal or metal alloys for coating the metallic interconnect 14 include iron, cobalt, nickel, copper and alloys thereof. The metal coating on the metallic interconnect 14 could be deposited by sputtering, physical vapor deposition and similar vapor processes or by means of electroplating or electroless plating.

In another example, electrode 12 may be strontium-doped lanthanum cobalt-doped ferrite (LSCF). In another example, the electrode 12 may be comprised of LSM, as the electronic conductor phase, and doped-zirconia or doped-ceria as the oxygen ion conductor phase. In yet another example, the electrode 12 may be comprised of LSCF, as the electronic conductor phase, and doped-zirconia or doped-ceria as the oxygen ion conductor phase. In yet another example, the electrode 12 could be strontium-doped lanthanum nickel-doped ferrite. In general, the electrode 12 could be a single ceramic oxide composition that exhibits mixed ionic and electronic conductivity (MIEC) or composite materials comprised of electronic and ionic conductor phases that are formulated to provide continuous ion and electron paths through the thickness of the ceramic electrode.

Figure 2A:
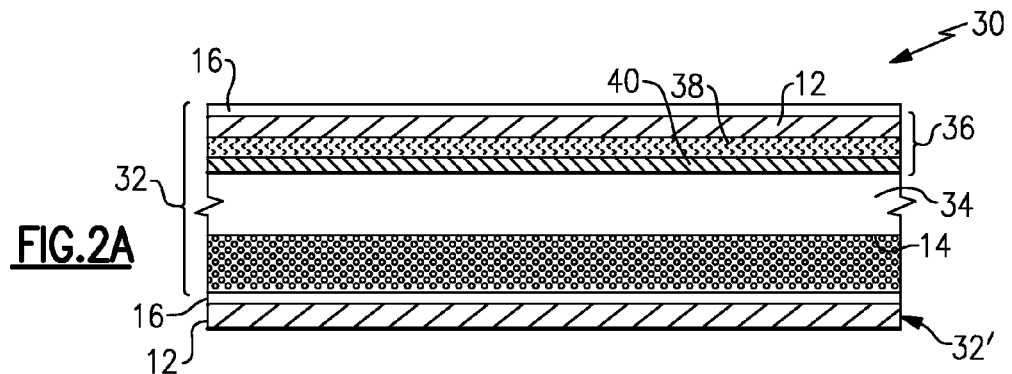
FIG. 2A illustrates an example fuel cell assembly that includes a ceramic bond material.

FIG. 2A illustrates selected portions of an example fuel cell assembly 30 that incorporates the ceramic bond material 16. In this example, the fuel cell assembly 30 includes a fuel cell unit 32 that operates in a known manner to generate electricity. As is known, multiple fuel cell units 32 may be stacked and sandwiched between collector plates (not shown) in an arrangement with an external circuit. However, it is to be understood that this disclosure is not limited to the arrangement of the example fuel cell assembly 30, and the concepts disclosed herein may apply to other fuel cell arrangements.

The exemplary fuel cell unit 32 includes a metallic support 34 between a planar solid oxide fuel cell 36 and the metal interconnect 14 (i.e., cathode interconnect). For instance, the metallic support may be a rigidized foil support or other suitable support that is adapted to deliver fuel to the fuel cell 36. The metal interconnect 14 may be configured to deliver oxidant to the fuel cell 36 of the assembly 30.

Figure 2B:
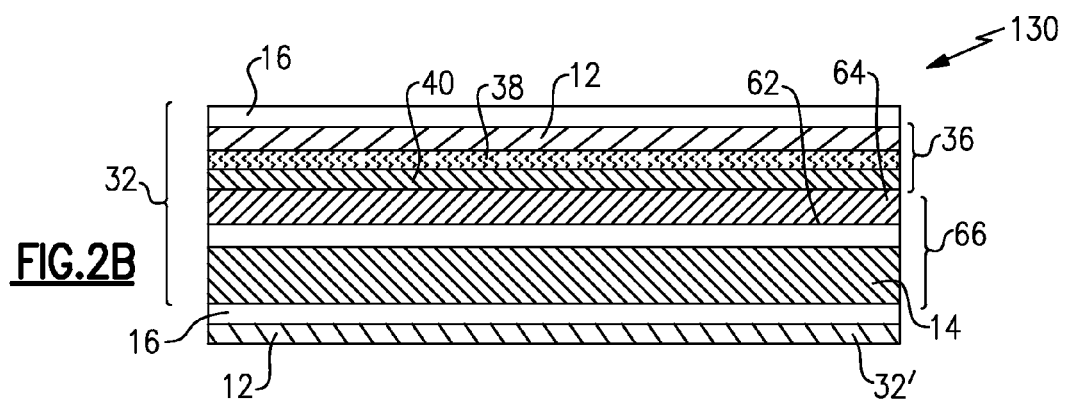
FIG. 2B illustrates another example of a fuel cell assembly that includes a ceramic bond material.

FIG. 2B illustrates selected portions of another example fuel cell assembly 130 that incorporates the ceramic bond material 16. In this example, the fuel cell assembly 130 includes a fuel cell unit 32 that operates in a known manner to generate electricity. The alternate fuel cell unit 32 includes a self-supporting fuel cell 36 adjacent to bipolar plate 66, wherein said bipolar plate is comprised of an anode interconnect 64, a separator plate 62, and a cathode interconnect 14. An exemplary bipolar plate 66 is comprised of one or more metals or metal alloys that are bonded together by metallurgical bonds (or joints) to form a single structure. Preferred materials of construction for the bipolar plate are a ferritic stainless steel for the separator plate 62, wherein the ferritic stainless steel is chosen to have a thermal expansion coefficient that is close to that of the fuel cell unit 32, while the interconnects 64 and 14 may be made of the same ferritic stainless steel or other metals or alloys that offer longer durability and electronic conductivity in the corrosive environment of the solid oxide fuel cell than the ferritic stainless steel. For example, the anode interconnect 64 may be made of nickel, copper or their alloys, while the cathode interconnect 14 may be made of oxidation resistant nickel-based alloys like Inconel or Hastalloy or Haynes 230™. Interconnect 14 may also be coated with appropriate ceramic oxide materials, having the crystalline structure of spinels or perovskites, which help to minimize or eliminate chromium oxide evaporation and/or improve the oxidation resistance of the metallic interconnect 14.

The fuel cell 36 may be a tri-layered arrangement, including a solid oxide electrolyte 38 between the ceramic electrode 12 and an anode electrode 40. In this case, the ceramic electrode 12 is a cathodic electrode. The solid oxide electrolyte 38 may be any type of solid oxide electrolyte, such as ceria ($CeO_2$) doped with rare earth metal oxide(s), gallate (e.g., strontium-doped lanthanum gallate) or stabilized (fully or partially) zirconia.

In a stack, the fuel cell unit 32 repeats such that the metal interconnect 14 is adjacent to the ceramic electrode 12 of a neighboring fuel cell unit 32' (shown in part). The ceramic bond material 16 bonds the metal interconnect 14 and the ceramic electrode 12 together, as discussed above relative to FIG. 1.

Figure 3:
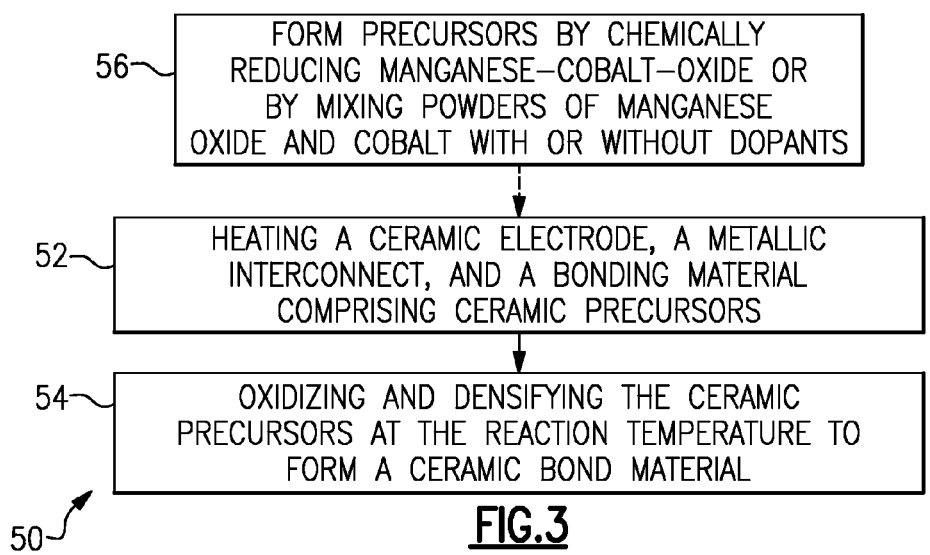
FIG. 3 illustrates an example method of processing an electrochemical device.

FIG. 3 illustrates an example method 50 of processing the electrochemical device 10, or the fuel cell assemblies 30 or 130. In this example, the method 50 includes a heating step 52 and an oxidizing/densifying step 54. Optionally, the method 50 may also include a preparation step 56 prior to the heating step 52 for preparing ceramic precursors to form the ceramic bond material 16. For instance, the ceramic precursors that will eventually form the ceramic bond material 16 may be prepared by chemically reducing a manganese-cobalt-oxide starting material, wherein the manganese-cobalt-oxide is a ceramic oxide material having a spinel crystal structure, or by mixing powders of manganese oxide and cobalt together. Similarly, ceramic bond material 16 doped with RE metals or REO as discussed hereandabove can be prepared by chemically reducing a corresponding doped manganese-cobalt-oxide starting material or by mixing powders of manganese oxide and cobalt and the dopant RE metals or cobalt-RE metal alloys together. Similarly, ceramic bond material 16 doped with transition metal oxides as discussed here and above can be prepared by chemically reducing a corresponding doped manganese-cobalt-oxide starting material or by mixing powders of manganese oxide and cobalt and the dopant transition metals together or by mixing powders of manganese oxide and cobalt-transition metal alloys together.

In one example of chemically reducing a manganese-cobalt-oxide starting material, the starting material may be applied to the ceramic electrode 12, the metallic interconnect 14, or both components and then chemically reduced to form manganese oxide and cobalt. The starting material may be applied in a known manner, such as by dipping, spraying, electrophoretic deposition or other known method with the starting material in a suitable carrier (e.g., an organic solvent). The carrier may be thermally removed after application to the component(s). The reduction reaction results in a volume contraction as the starting material reduces to mangansese oxide and a metal composition, for example, cobalt in the case of pure or non-doped manganese cobalt oxide. The ceramic electrode 12 and the metallic interconnect 14 may be pressed together, with the starting material in between, to facilitate avoiding gaps from the volume contraction.

The chemical reduction may be conducted in an atmosphere comprised of inert gas, hydrogen, and water vapor at a temperature below about 950° C. As an example, the temperature may be around 800° C., and optionally as low as about 700° C., and results in nanosized particles of the manganese oxide and cobalt in the case of pure or non-doped manganese cobalt oxide. The nanosized particles may later provide the benefit of high chemical activity during the oxidizing/densifying step 54. As an example, "nanosized" may refer to particles that are one-hundred nanometers or less in size.

Alternatively, the manganese-cobalt-oxide starting material may be reduced separately from the ceramic electrode 12 and the metallic interconnect 14 and then applied to the components in a similar manner as described above. Equation 1 below shows an example overall reduction reaction of the manganese-cobalt-oxide spinel starting material.

$$Mn_{1.5}Co_{1.5}O_4 + 2.5H_2 \rightarrow 1.5MnO + 1.5Co + 2.5H_2O \qquad (1)$$

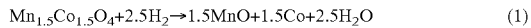

Alternatively, the ceramic precursors may be prepared by mixing powders of manganese-oxide and cobalt together and then applying the mixture to the ceramic electrode 12 and/or the metallic interconnect 14 in a similar manner as described above. As an example, the particles of the manganese oxide and/or the cobalt may be nanosized to promote chemical activity during the later oxidizing/densifying step 54. If dopants or other materials are to be included in the composition, as discussed above, the dopant or other material may also be added to the powder mixture.

The ceramic precursors may be arranged between the ceramic electrode 12 and the metallic interconnect 14 in preparation for forming the ceramic bond material 16. Alternatively, the manganese-cobalt-oxide starting material may be arranged between the ceramic electrode 12 and the metallic interconnect 14 for forming the ceramic precursors in situ, as described above. In some examples, the ceramic electrode 12 and the metallic interconnect 14 may be pressed together to exert a compressive force on the ceramic precursors during the oxidizing/densifying step 54.

The assembly of the ceramic electrode 12, the metallic interconnect 14, and the ceramic precursors is then heated in the heating step 52 to a reaction temperature. For instance, the reaction temperature may be less than about 950° C. In some examples, the reaction temperature may be less than about 800° C., and as low as about 700° C. The heating step 52 may be conducted in an oxygen-containing atmosphere, such as air, to oxidize and densify the ceramic precursors. As an example, Equation 2 below shows the overall oxidation reaction of manganese-oxide and cobalt to manganese cobalt oxide spinel.

$$1.5MnO + 1.5Co + 1.25O_2 \rightarrow Mn_{1.5}Co_{1.5}O_4 \qquad (2)$$

The precursors are comprised of ceramic and metallic phases as exemplified by the left-hand side of Eq. 2. During oxidation the metallic phase forms oxides with simultaneous very large volume expansion and the oxide phase is formed initially as nanoscale oxide particles that have very high reactivity. Without any assertion of describing all the physical phenomena that occur during the oxidation step, the reactivity of the newly formed nanoscale oxide particles and the large volume expansion, promote particle growth, particle rearrangement and porosity expulsion which lead to densification of the bond material and development of a high strength bond between the metallic interconnect 14 and the ceramic electrode 12 at temperatures below 950° C. The low temperature of step 54 mitigates oxide scale formation on interconnect 14, which in turn reduces the electric resistance of current flow between interconnect 14 and ceramic electrode 12. Other ceramic compositions, such as perovskite compositions, sinter at much higher temperatures, higher than 1100° C., that would melt, oxidize, or otherwise damage the metallic interconnect 14. Thus, the ceramic precursors of this disclosure provide the benefit of densifying, or consolidating into a porous coherent mass by heating without melting, at a low temperature that does not damage the metallic interconnect 14 and forming a high strength bond between the ceramic electrode 12 and the metallic interconnect 14. As an example, the bond strength of the ceramic bond material 16 may be greater than the bond strength between the ceramic electrode 12 and the solid oxide electrolyte 38 (or a barrier layer between the ceramic electrode 12 and the solid oxide electrolyte 38).

The ceramic precursors oxidize and densify to form the ceramic bond material 16. The prior reduction of the manganese-cobalt-oxide starting material results in a reduction in the volume of the material, while the oxidation results in volume expansion. As an example, the expansion may be around 70 vol % relative to the ceramic precursors. The expansion allows rearrangement of metal ions and inter-diffusion that facilitates densification. Thus, the volume change and relatively small size of the precursor particles drive densification such that a porous coherent material results at the relatively low reaction temperature, less than 950° C., of the heating step 52. Also, the expansion may reduce the need to use high pressing forces between the ceramic electrode 12 and the metallic interconnect 14 during densification because there is no contraction as in traditional sintering.

The method 50 may be modified to tailor the ceramic bond material 16 for the particular needs of an application. For instance, the ceramic precursors may include processing agents for controlling the porosity of the ceramic bond material 16. Also, the atmosphere during the heating step 52 may be controlled to control the oxidation and/or densification of the ceramic precursors to achieve a desired structure, composition, or properties of the ceramic bond material 16, for example.

As a further example, an electrochemical test using a bonding material of $Mn_{1.5}Co_{1.5}O_4$ and a round anode supported cell (ASC) was performed to evaluate efficacy and compatibility of the material. A radial module with seal-less design was employed. Fuel and air entered the radial module from the center of fuel and air endplates (stainless steel 430), respectively, and exited the module from its circular peripheral. A corrugated cathode interconnect (cathode current collector) was made by specially forming a piece of Haynes 230 (H230) wire mesh and the corrugated cathode interconnect was spot welded to the cathode endplate to maintain metallurgical bonding. Flat nickel mesh was used as the anode current collector and it was bonded to cell anode electrode by means of NiO paste, which is converted to Ni after firing and reduction.

In this example, powder of the bonding material $Mn_{1.5}Co_{1.5}O_4$ was reduced in 4% H2/N2 at 750° C. to form a reduced powder precursor. The reduced powder precursor was subsequently mixed with V-006 and RV-372 (V-006 and RV-372 are commercial materials marketed by Heraeus) to make the bond paste. An amount of 0.079 $g/cm^2$ of bond paste was evenly applied onto the cathode surface of an ASC. The radial module was clamped to a desirable compression to maintain good electrical contact of the assembly. The single cell radial module was placed in a furnace for firing and testing. Prior to electrochemical testing, heat treatment was carried out in flowing air to oxidize the reduced powder precursor and to form strong bonding between the cathode electrode and the cathode current collector. A typical protocol of such a heat treatment is presented in Table 1. The cell anode electrode and NiO bond paste was reduced subsequently to the heat treatment, while electrochemical testing followed both the heat treatment and reduction steps.

TABLE 1

Heat treatment protocol for bonding cathode interconnect to cathode in

| Step | Initial Temp. (° C.) | Final Temp. (° C.) | Duration (min) | Rate (° C./min) |
|---|---|---|---|---|
| Heating | 20 | 350 | 110 | 3 |
| Holding | 0 | 0 | 120 | |
| Heating | 350 | 850 | 50 | 10 |
| Holding | 0 | 0 | 120 | |
| Cooling | 850 | 750 | 20 | 5 |

Figure 4:
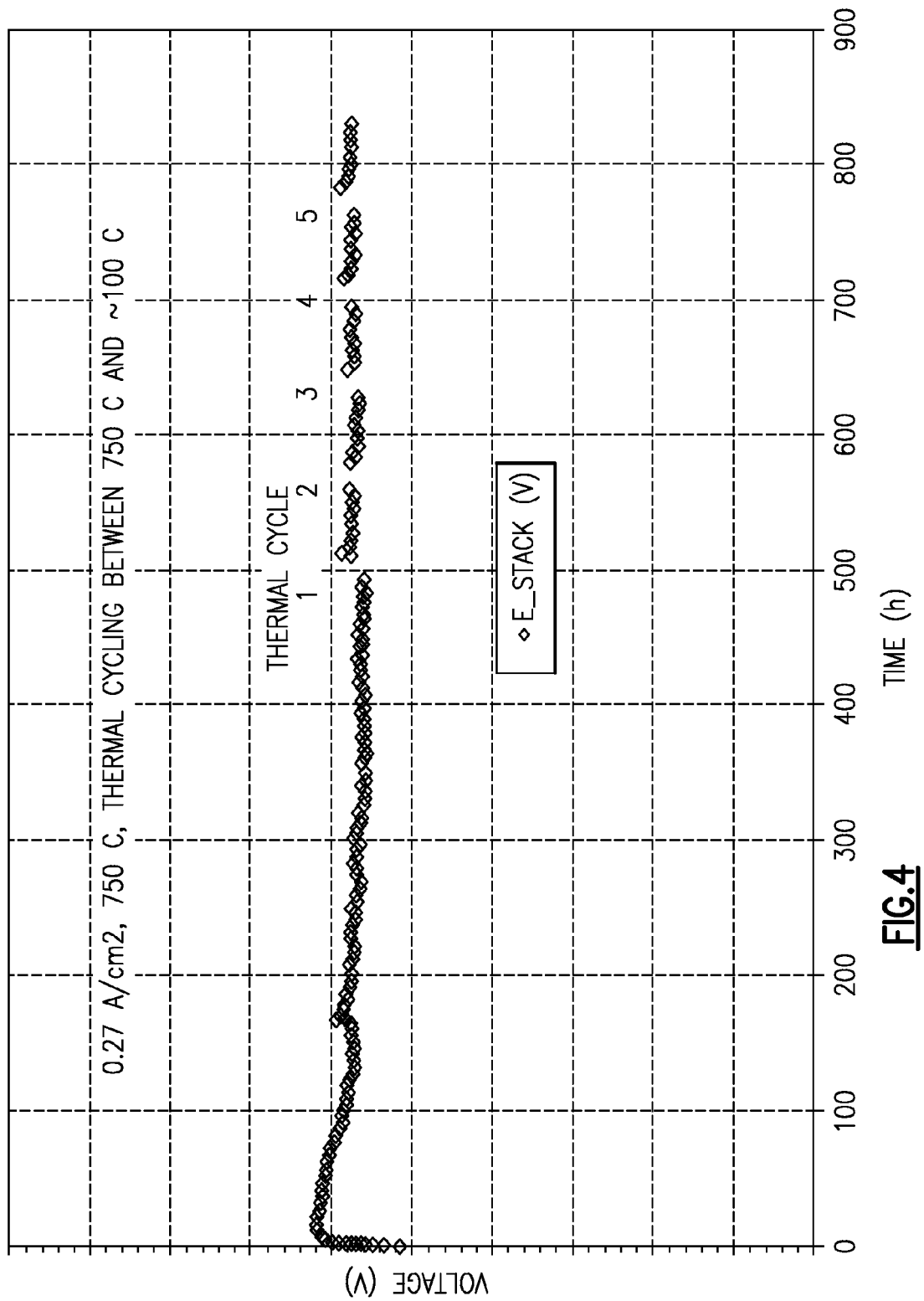
FIG. 4 illustrates a graph of voltage versus time.

Once the cell performance stabilized, thermal cycling tests were performed as follows with the cell placed under open circuit potential by ramping the electrical load down before each thermal cycle. The furnace was cooled down at 3° C./min to room temperature, followed by heating up the furnace at 3° C./min to 750° C./min. Current (0.27 $A/cm^2$) was applied and the cell was held at constant current condition for 10 hours before the next thermal cycle. FIG. 4 shows the module voltage with time during constant temperature (segment from 0 hours to about 500 hours) and thermal cycling tests (segment from 500 hours to about 840 hours). It is seen that cell performance exhibited no loss during the thermal cycling, confirming the robustness of interconnect/cathode bond despite thermal expansion mismatch between H230 mesh interconnect and cell.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from the essence of this disclosure.

The scope of legal protection given to this disclosure can only be determined by studying the following claims.

What is claimed is:

1. An electrochemical device comprising:
a ceramic electrode;
a metallic interconnect; and
a ceramic bond material that bonds the ceramic electrode and the metallic interconnect together, the ceramic bond material comprising manganese-cobalt-oxide that is electrically conductive such that electric current can flow between the ceramic electrode and the metallic interconnect, wherein the ceramic electrode comprises strontium-doped lanthanum manganite and the metallic interconnect comprises nickel-based alloy coated with manganese cobalt ferrite with or without dopants.

2. The electrochemical device as recited in claim 1, wherein the manganese-cobalt-oxide comprises $Mn_{1.5}Co_{1.5}O_4$.

3. The electrochemical device as recited in claim 1, wherein the manganese-cobalt-oxide comprises $Mn_2CoO_4$.

4. The electrochemical device as recited in claim 1, wherein the manganese-cobalt-oxide comprises $MnCo_2O_4$.

5. The electrochemical device as recited in claim 1, wherein the manganese-cobalt-oxide comprises $Mn_2CoO_4$ and $MnCo_2O_4$.

6. The electrochemical device as recited in claim 1, wherein the ceramic bond material includes a dopant selected from a group consisting of rare earth elements and mixtures thereof.

7. The electrochemical device as recited in claim 1, wherein the ceramic bond material includes a ceria dopant.

8. The electrochemical device as recited in claim 1, wherein the ceramic bond material includes a dopant selected from a group consisting of rare earth oxides and mixtures thereof.

9. The electrochemical device as recited in claim 1, wherein the ceramic bond material includes a dopant selected from a group consisting of iron, chromium, nickel, copper, zinc, zinc oxide, and mixtures thereof.

10. The electrochemical device as recited in claim 1, wherein the ceramic bond material is in direct contact with the ceramic electrode and the metallic interconnect.

11. An electrochemical device comprising:
a ceramic electrode;
a metallic interconnect; and
a ceramic bond material that bonds the ceramic electrode and the metallic interconnect together, the ceramic bond material comprising manganese-cobalt-oxide that is electrically conductive such that electric current can flow between the ceramic electrode and the metallic interconnect, wherein the ceramic electrode comprises strontium-doped lanthanum cobalt-doped ferrite and the metallic interconnect comprises nickel-based alloy coated with manganese cobalt ferrite with or without dopants.

12. The electrochemical device as recited in claim 11, wherein the manganese-cobalt-oxide comprises $Mn_{1.5}Co_{1.5}O_4$.

13. The electrochemical device as recited in claim 11, wherein the manganese-cobalt-oxide comprises $Mn_2CoO_4$.

14. The electrochemical device as recited in claim 11, wherein the manganese-cobalt-oxide comprises $Mn_2CoO_4$.

15. The electrochemical device as recited in claim 11, wherein the manganese-cobalt-oxide comprises $Mn_2CoO_4$ and $MnCo_2O_4$.

16. The electrochemical device as recited in claim 11, wherein the ceramic bond material includes a dopant selected from a group consisting of rare earth elements and mixtures thereof.

17. The electrochemical device as recited in claim 11, wherein the ceramic bond material includes a ceria dopant.

18. The electrochemical device as recited in claim 11, wherein the ceramic bond material includes a dopant selected from a group consisting of rare earth oxides and mixtures thereof.

19. The electrochemical device as recited in claim 11, wherein the ceramic bond material includes a dopant selected from a group consisting of iron, chromium, nickel, copper, zinc, zinc oxide, and mixtures thereof.

20. The electrochemical device as recited in claim 11, wherein the ceramic bond material is in direct contact with the ceramic electrode and the metallic interconnect.

* * * * *

UNITED STATES PATENT AND TRADEMARK OFFICE
CERTIFICATE OF CORRECTION

| | | |
|---|---|---|
| PATENT NO. | : 9,120,683 B2 | Page 1 of 1 |
| APPLICATION NO. | : 13/577327 | |
| DATED | : September 1, 2015 | |
| INVENTOR(S) | : Jean Yamanis et al. | |

It is certified that error appears in the above-identified patent and that said Letters Patent is hereby corrected as shown below:

Specification

<u>Column 1, Line 5, Insert:</u>
--STATEMENT REGARDING FEDERALLY SPONSORED RESEARCH OR DEVELOPMENT
This invention was made with government support under Contract No. DE-NT0003894 awarded by the Department of Energy. The Government therefore has certain rights in this invention.--.

Signed and Sealed this
Twenty-first Day of June, 2016

Michelle K. Lee
*Director of the United States Patent and Trademark Office*